United States Patent
Palanker et al.

(10) Patent No.: US 9,192,518 B2
(45) Date of Patent: Nov. 24, 2015

(54) SYSTEM FOR TREATING OPHTHALMIC TARGET TISSUE USING A TREATMENT PATTERN OF LESIONS

(71) Applicant: Topcon Medical Laser Systems, Inc., Santa Clara, CA (US)

(72) Inventors: Daniel V. Palanker, Sunnyvale, CA (US); Dan Andersen, Menlo Park, CA (US)

(73) Assignee: TOPCON MEDICAL LASER SYSTEMS, INC., Santa Clara, CA (US)

(*) Notice: Subject to any disclaimer, the term of this patent is extended or adjusted under 35 U.S.C. 154(b) by 0 days.

(21) Appl. No.: 14/195,106

(22) Filed: Mar. 3, 2014

(65) Prior Publication Data
US 2014/0207127 A1 Jul. 24, 2014

Related U.S. Application Data

(60) Division of application No. 13/691,691, filed on Nov. 30, 2012, now Pat. No. 8,672,924, which is a continuation of application No. 11/939,398, filed on Nov. 13, 2007, now Pat. No. 8,336,555.

(60) Provisional application No. 60/857,951, filed on Nov. 10, 2006.

(51) Int. Cl.
*A61B 18/18* (2006.01)
*A61F 9/008* (2006.01)
(Continued)

(52) U.S. Cl.
CPC ............... *A61F 9/008* (2013.01); *A61B 18/20* (2013.01); *A61F 9/00821* (2013.01);
(Continued)

(58) Field of Classification Search
CPC ....... A61F 9/007; A61F 9/0079; A61F 9/008; A61F 9/00802; A61F 9/00821; A61F 9/00825; A61F 9/00827; A61F 2009/00853; A61F 2009/00897; A61B 18/00; A61B 18/04; A61B 18/20
USPC .......................... 606/4–6, 10–12; 607/88, 89
See application file for complete search history.

(56) References Cited

U.S. PATENT DOCUMENTS

| 4,917,486 A | 4/1990 | Raven et al. |
| 6,099,521 A | 8/2000 | Shadduck |

(Continued)

FOREIGN PATENT DOCUMENTS

| WO | 2005/007002 A1 | 1/2005 |
| WO | 2006/005038 A2 | 1/2006 |
| WO | 2006/091890 A2 | 8/2006 |

OTHER PUBLICATIONS

Extended European Search Report received for EP Patent Application No. 07861943.4, mailed on Dec. 6, 2010, 6 pages.
(Continued)

*Primary Examiner* — Ahmed Farah
(74) *Attorney, Agent, or Firm* — Morrison & Foerster LLP

(57) ABSTRACT

A system and method for treating ophthalmic target tissue, including a light source for generating a beam of light, a beam delivery system that includes a scanner for generating patterns, and a controller for controlling the light source and delivery system to create a dosimetry pattern of the light beam on the ophthalmic target tissue. One or more dosage parameters of the light beam vary within the dosimetry pattern, to create varying exposures on the target tissue. A visualization device observes lesions formed on the ophthalmic target tissue by the dosimetry pattern. The controller selects dosage parameters for the treatment beam based upon the lesions resulting from the dosimetry pattern, either automatically or in response to user input, so that a desired clinical effect is achieved by selecting the character of the lesions as determined by the dosimetry pattern lesions.

7 Claims, 6 Drawing Sheets

(51) Int. Cl.
*A61B 19/00* (2006.01)
*A61B 18/20* (2006.01)

(52) U.S. Cl.
CPC .... *A61B 19/5212* (2013.01); *A61B 2018/2085* (2013.01); *A61F 2009/00855* (2013.01); *A61F 2009/00863* (2013.01); *A61F 2009/00868* (2013.01); *A61F 2009/00897* (2013.01)

(56) References Cited

U.S. PATENT DOCUMENTS

| | | | |
|---|---|---|---|
| 6,099,522 | A | 8/2000 | Knopp et al. |
| 6,149,643 | A | 11/2000 | Herekar et al. |
| 6,913,603 | B2 | 7/2005 | Knopp et al. |
| 7,146,983 | B1 | 12/2006 | Hohla et al. |
| 7,364,574 | B2 | 4/2008 | Flower |
| 7,766,903 | B2 | 8/2010 | Blumenkranz et al. |
| 8,187,257 | B2 | 5/2012 | Lin et al. |
| 8,336,555 | B2 | 12/2012 | Palanker et al. |
| 8,366,704 | B2 * | 2/2013 | Lin et al. ............ 606/10 |
| 8,734,433 | B2 * | 5/2014 | Palanker et al. ........ 606/4 |
| 2002/0036750 | A1 | 3/2002 | Eberl et al. |
| 2002/0099363 | A1 * | 7/2002 | Woodward et al. ......... 606/5 |
| 2006/0100677 | A1 | 5/2006 | Blumenkranz et al. |
| 2006/0111697 | A1 | 5/2006 | Brinkmann et al. |
| 2006/0161145 | A1 | 7/2006 | Lin et al. |
| 2006/0217691 | A1 | 9/2006 | Schuele et al. |
| 2007/0129709 | A1 | 6/2007 | Andersen et al. |
| 2009/0093798 | A1 * | 4/2009 | Charles ............ 606/4 |
| 2011/0282333 | A1 * | 11/2011 | Herekar et al. ......... 606/5 |

OTHER PUBLICATIONS

Extended European Search Report and Search Opinion received for Patent Application No. 12158325.6, mailed on May 9, 2012, 5 pages.
International Search Report and Written Opinion received for PCT patent Application No. PCT/US2007/023730, mailed on May 23, 2008, 7 page.
International Preliminary Report on Patentability received for PCT Patent Application No. PCT/US2007/023730, issued on May 12, 2009, 7 pages.
Office Action received for Australian Patent Application No. 2011203543, mailed on Feb. 22, 2012, 2 pages.
Decision to Grant received for Japanese Patent Application No. 2009-535367, mailed on Mar. 21, 2013, 3 pages of Official Copy Only (See Communication under 37 CFR § 1.98(a) (3)).

* cited by examiner

SYSTEM FOR TREATING OPHTHALMIC TARGET TISSUE USING A TREATMENT PATTERN OF LESIONS

CROSS-REFERENCES TO RELATED APPLICATIONS

This application is a divisional of U.S. Non-provisional application Ser. No. 13/691,691, filed Nov. 30, 2012, which is a continuation of U.S. Non-provisional application Ser. No. 11/939,398, filed Nov. 13, 2007, now U.S. Pat. No. 8,336,555, which claims the benefit of U.S. Provisional Application No. 60/857,951, filed Nov. 10, 2006. The content of the above-referenced applications is incorporated herein by reference for all purposes.

FIELD OF THE INVENTION

A system and method for determining dosimetry for photothermal treatment of ocular structures, for example, the retinal pigmented epithelium, photoreceptors, and other retinal layers, and those of the trabecular meshwork. It is particularly useful in the treatment of a variety of retinal disorders, as well as ocular hypertension.

BACKGROUND OF THE INVENTION

Laser photomedicine is a well-established therapeutic modality for a wide variety of conditions. To date, the use of ophthalmic lasers has been limited to either short (around one microsecond or shorter) pulse systems for sub-cellular targeting, or long (hundreds of microseconds and longer) pulse systems that indiscriminately denature relatively large volumes of tissue.

For example, present standard retinal photocoagulative treatment for conditions such as Diabetic Retinopathy, and Age-Related Macular Degeneration utilize visible laser light with exposure durations on the order of 100 ms. Generation of heat due to absorption of visible laser light occurs predominantly in the retinal pigmented epithelium (RPE) and pigmented choriocappilaris, the melanin containing layers directly beneath the photoreceptors of the sensory retina. The RPE is disposed between the sensory retina and the choroid. Due to heat diffusion during long exposures, this standard therapy also irreversibly damages the overlying sensory retina.

Although it does halt the progress of the underlying disease, such irreversible damage decreases the patient's vision by destroying not only the photoreceptors in the irradiated portion of the retina but also by creating permanent microscotomas, and possibly also damaging the retinal nerve fibers that traverse the targeted portion of the retina, creating a defect called arc scotoma. Such nerve fiber damage eliminates the signals it would have carried from distal areas of the retina, thus unnecessarily further worsening the patient's vision.

To address these issues, systems and methods for creating spatially confined photothermal lesions in ocular tissues have been proposed, such as in co-pending U.S. patent application Ser. No. 11/606,451, which is incorporated herein by reference. However, what is lacking in such systems and methods is a means for gauging a patient's idiosyncratic response and for reliable delivery of the treatment light to create lesions in response thereto.

Due to strong variability of the retinal absorption, ocular transmission of light, and choroidal blood perfusion, the laser-induced retinal temperature rise strongly varies from patient to patient, and even from location to location in a single patient. So, a global parameter setting for a desired clinical result is not ideal. Left uncorrected, these differences can lead to inhomogeneous treatments, over-treating in some areas and under-treating in others. Physicians have traditionally determined the appropriate treatment for each patient (and even for different areas in the retina of the same patient) by a "trial and error" approach, which takes a significant amount of time and is entirely qualitative.

Accordingly, there is a need for a rapid, robust, and cost-effective system and method for providing predictable ophthalmic photomedical treatment such as, but not limited to, the retina and trabecular meshwork, that is not provided by known methods or devices.

SUMMARY OF THE INVENTION

The present invention solves the aforementioned problems by providing a system and method for treating ophthalmic target tissue using a "dosimetry pattern" of light of varying pulse durations, spot sizes and/or power densities to efficiently determine the photothermal target properties, and provide more predictable treatment results. The dosimetry pattern may be a plurality of fixed spots, one or more continuous scans resulting in one or more straight or curved line segments, or a combination of both. By locating the region within the dosimetry pattern that provides a visible lesion of a desirable character, or extrapolating such a region, the operating physician may then choose the appropriate system parameters for a given treatment. Alternately, the photomedical system may incorporate an imaging system that identifies the lesions within the dosimetry pattern with the desired clinical results, and adjusts the system parameters in an automated fashion.

A system for treating ophthalmic target tissue includes a light source for generating a beam of light, a beam delivery unit for delivering the beam of light to ophthalmic target tissue, wherein the beam delivery unit includes a scanner unit for deflecting the beam of light, a controller for controlling at least one of the light source and the beam delivery unit to create a dosimetry pattern of the beam of light on the ophthalmic target tissue for which at least one dosage parameter of the beam of light varies within the dosimetry pattern, and a visualization device for capturing an image of lesions formed on the ophthalmic target tissue by the dosimetry pattern. The controller is configured to control at least one of the light source and the beam delivery unit to then deliver the beam of light to the ophthalmic target tissue having at least one dosage parameter thereof selected in response to the captured image of lesions.

A method of treating ophthalmic target tissue includes generating a beam of light, delivering the beam of light to ophthalmic target tissue using a scanner unit for deflecting the beam of light, creating a dosimetry pattern of the beam of light on the ophthalmic target tissue for which at least one dosage parameter of the beam of light varies within the dosimetry pattern, capturing an image of lesions formed on the ophthalmic target tissue by the dosimetry pattern, selecting at least one dosage parameter for the beam of light in response to the captured image of lesions, and delivering the beam of light to the ophthalmic target tissue having the selected at least one dosage parameter.

In another aspect, a system for treating ophthalmic target tissue includes a light source for generating a beam of light, a beam delivery unit for delivering the beam of light to ophthalmic target tissue, wherein the beam delivery unit includes a scanner unit for deflecting the beam of light, a controller for controlling at least one of the light source and the beam delivery unit to create a dosimetry pattern of the beam of light on the ophthalmic target tissue for which at least one dosage parameter of the beam of light varies within the dosimetry pattern, a visualization apparatus for observing lesions formed on the ophthalmic target tissue by the dosimetry pattern, and a user interface for receiving information about the observed lesions. The controller is configured to control at least one of the light source and the beam delivery unit to then deliver the beam of light to the ophthalmic target tissue having at least one dosage parameter thereof selected in response to the received information.

In yet one more aspect, a method for treating ophthalmic target tissue includes generating a beam of light using a light source, delivering the beam of light to ophthalmic target tissue using a beam delivery unit having a scanner unit for deflecting the beam of light, creating a dosimetry pattern of the beam of light on the ophthalmic target tissue for which at least one dosage parameter of the beam of light varies within the dosimetry pattern, observing lesions formed on the ophthalmic target tissue by the dosimetry pattern, entering information about the observed lesions using a user interface that is connected to a controller that controls at least one of the light source and the beam delivery unit, selecting at least one dosage parameter for the beam of light in response to the entered information, and controlling at least one of the light source and the beam delivery unit using the controller to then deliver the beam of light to the ophthalmic target tissue having the at least one selected dosage parameter.

Other objects and features of the present invention will become apparent by a review of the specification, claims and appended figures.

DETAILED DESCRIPTION OF THE PREFERRED EMBODIMENTS

The present invention is a system and method for the efficient determination of treatment parameters needed to form desired ophthalmic photothermal lesions, which allows for the proper setting and adjustment of the treatment parameters. The system operates based on the visible response of the target tissue to a dosimetry pattern of light which creates lesions on the target tissue. Tissue appearance following its exposure to the dosimetry pattern helps the system and/or user to select appropriate system settings for subsequent treatment. A specific lesion exhibiting the character to produce the desired clinical effect may be identified and corresponding system settings used, or the settings may be extrapolated from the observation of the results of the dosimetry pattern.

Figure 1:
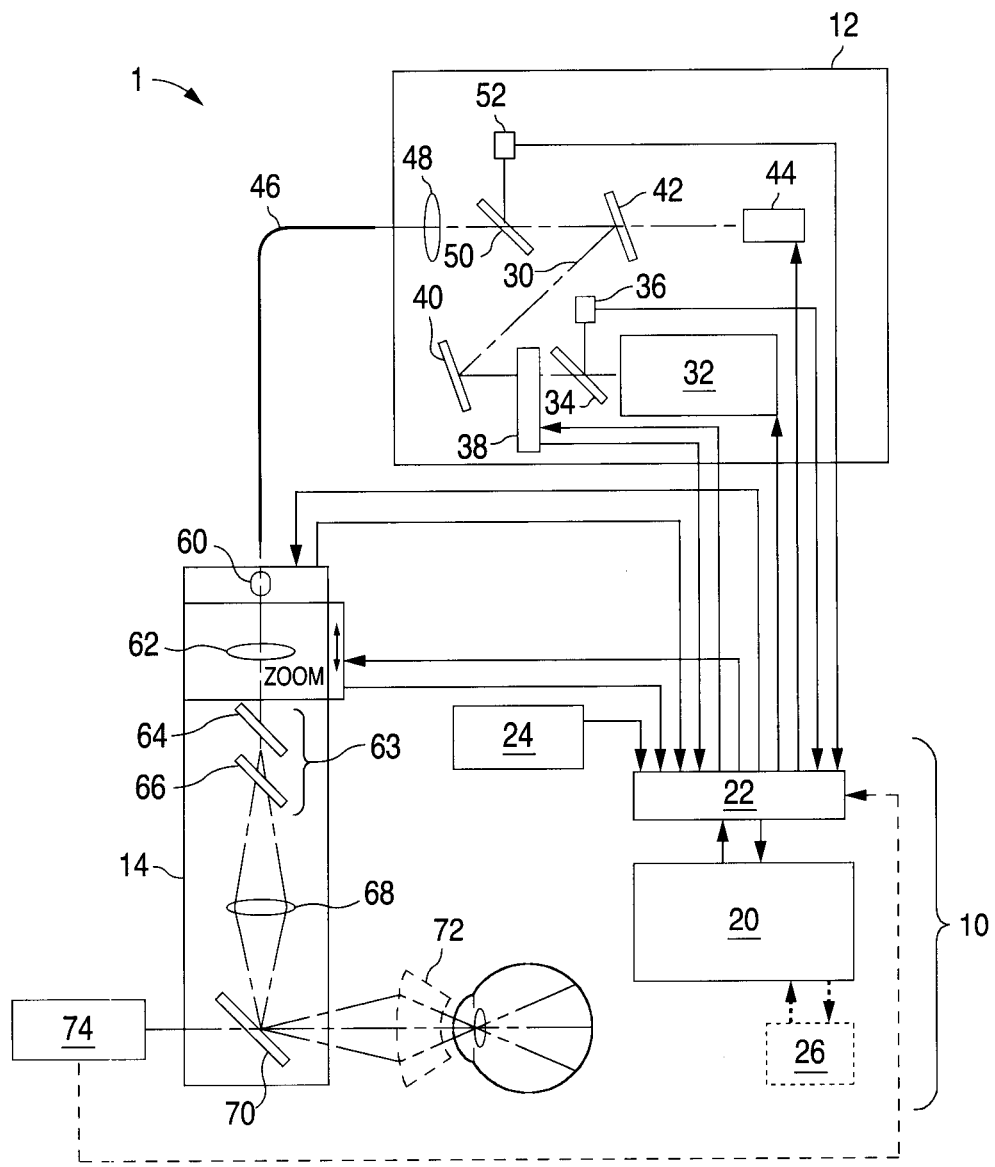
FIG. 1 is a schematic diagram illustrating a system for retinal treatment.

FIG. 1 illustrates a system 1 for implementing ophthalmic photothermal treatment, which includes a control unit 10, a light generation unit 12 and a light delivery unit 14. This system can provide either pulses of light, or continuous scans of light, to the eye of a patient. The pulse duration, laser power density and the spot size on tissue all affect the exposure of the tissue to the treatment light (i.e. the dosage of light for the tissue), and thus characteristics of the lesions formed thereby. The control unit 10 controls the disposition (generation and delivery) of the light, and includes control electronics (i.e. a controller) 20 and an input and output 22. Likewise, input from an input device 24 (e.g. a joystick) and/or a graphic user interface (GUI) 26, may be used by the control electronics 20 for controlling the light disposition.

In the light generation unit 12, a light beam 30 is generated by a light source 32, such as a 532 nm wavelength frequency-doubled, diode-pumped solid state laser. The beam 30 first encounters a mirror 34 which serves to monitor the light for safety purposes, reflecting a fixed portion towards a photodiode 36 that measures its power. Following that, the light beam 30 encounters a shutter 38, mirror 40, and mirror 42. Shutter 38 controls the delivery of the light beam 30. It may also be used to gate the light, in addition to grossly blocking it. Mirror 40 is configured as a turning mirror as well as a combining mirror to combine aiming light from a second light source 44 with light beam 30. The aiming light is preferably aligned along the same path as the light beam 30 to provide a visual indication of where the treatment light from source 32 will be projected onto the target tissue. After mirror 42, the light beam 30 (now including aiming light from source 44) is directed into an optical fiber 46 via a lens 48. An optional mirror 50 can be used to direct a portion of the light beam to a second photodiode 52, which serves purposes similar to those of mirror 34 and photodiode 36, as well as a redundant monitor of the state of shutter 38. Optical fiber 46 is a convenient way to deliver the light from the light generation unit 12 to the light delivery unit 14. However, free-space delivery of the light may be used instead, especially where the light generation and delivery units 12, 14 are integrally packaged together.

In the light delivery unit 14, lens 60 conditions the light exiting the optical fiber 46. Lens 60 may be a single lens, or a compound lens. If it is a compound lens, lens 60 may be a zoom lens that adjusts the spot diameter of the beam. This is useful for easy adjustment of the size of patterns and their elements on the target tissue as discussed further below. An additional lens 62 may be used to image the optical beam downstream, and possibly act as a zoom lens, as shown. The image point of lens 62 can be selected to minimize the size of optical elements downstream. A scanner 63, preferably having a pair of scanning optics (i.e. movable mirrors, wedges, and/or lenses), is used to deflect the beam 30 to form a pattern P of spots or lines (straight or curved). Preferably, the scanning optics rotate or move in orthogonal X, Y directions such that any desired pattern P can be produced. A lens 68 focuses the beam onto a mirror 70 which redirects the beam through an ophthalmic lens 72 and onto the target tissue. Mirror 70 can also be part of a visualization apparatus which provides for visualization of the target tissue therethrough, either directly by the physician or by a visualization device 74. More specifically, visualization may be accomplished by directly viewing the retina through mirror 70, or by capturing an image using a visualization device 74 (e.g. CCD camera) to be displayed either on a remote monitor, or, as indicated by the dashed line of FIG. 1, on the graphical user interface 26.

Ideally, the lens 62 images the beam to a midpoint between scanning optics 64, 66 and onto mirror 70. This may be done to minimize the size of the mirror 70 in an attempt to increase the overall solid angle subtended by the visualization device 74. When mirror 70 is small, it may be placed directly in the visualization path without much disturbance. It may also be placed in the center of a binocular imaging apparatus, such as a slit lamp biomicroscope, without disturbing the visualization. Lens 62 could also be placed one focal length away from the optical midpoint of the scanning optics 64, 66 to produce a telecentric scan. In this case, mirror 70 would need to be large enough to contain the entire scan, and could be made a high reflector spectrally matched to the output of light sources 32, 44, and visualization accomplished by looking through mirror 70. To photopically balance the transmission of mirror 70 (i.e. to make the colors of the tissue appear more natural), a more sophisticated optical coating can be used thereon instead of a simple green notch filter coating that produces pinkish images.

Ophthalmic lens 72 may be placed directly before the eye to aid in visualization, such as might be done with any ophthalmoscope, slitlamp biomicroscope, fundus camera, scanning laser ophthalmoscope (SLO), or optical coherence tomography (OCT) system, which together with mirror 70 and optional ophthalmic lens 72 form the desired configuration for a visualization device for direct physician visualization. Ophthalmic lens 72 may be a contact or non-contact lens, although a contact lens is preferred because it serves the additional purpose of dampening any of the patient's eye movement.

The dosimetry pattern P of light formed by the scanning optics 64, 66 can be a plurality of fixed spots, one or more continuous scans resulting in one or more straight or curved line segments, or a combination of both. Light sources 32, 44 and/or shutter 38 may be gated on and off by commands from control electronics 20 via input and output 22 to produce discrete spots, or simply run cw to create continuous scans as a means to produce dosimetry pattern P. Control electronics 20 likewise can also be configured to control the position of mirror 70 and therefore, ultimately, the dosimetry pattern P.

There are other techniques for creating dosimetry pattern P, such as by moving the light source(s) directly. Alternately, scanner 63 can comprise a two-dimensional acousto-optic deflector, or one or more optical elements with optical power that are translated. Mirror 70 may be tilted or translated (if there is surface curvature) to either act as the system scanner or augment beam movement already created by scanner 63. In the case where mirror 70 has optical power, compensating optical elements (not shown) may be required to produce an image, as opposed to a simple illumination. Similarly, the beam 30 could be divided using passive elements, such as diffractive optical elements (e.g. gratings or holograms), refractive elements (e.g. beam splitters, lenslet arrays, etc), or even active devices (e.g. adaptive optics) to create multiple beams simultaneously. These beams could then be deployed at once for faster treatment. They may also be used in conjunction with scanner 63 to provide a mixed approach.

Thus, the above described system 1 is configured to produce a dosimetry pattern P (of fixed spots or a moving beam) with varying dosages of light for different tissue areas within the dosimetry pattern P. Varying dosage can be achieved by varying the time the beam dwells on any given tissue location (either varying the time a fixed spot is applied to a particular tissue location, or varying the velocity a spot passing over a tissue location), varying the power density, and/or varying the spot size of the beam. Therefore, any given location of the target tissue will experience a dosage of light that depends upon the pulse duration, the power density, and the spot size of the light delivered to that location. At least one of these "dosage parameters" are thus varied within the dosimetry pattern P to create lesions exhibiting differing visual characteristics (e.g. size, color, darkness, etc.). Thus, the term "pulse duration" is used herein to describe the duration of exposure (i.e. the length of time light is applied to a given tissue location), including where the light beam is delivered to the target tissue without intentional motion for a particular time duration and where the light beam is made to move over the target tissue causing an exposure of a particular time duration. There are practical concerns, however, such as hand and eye movements that should be addressed to ensure precise treatment is provided.

Figure 2:
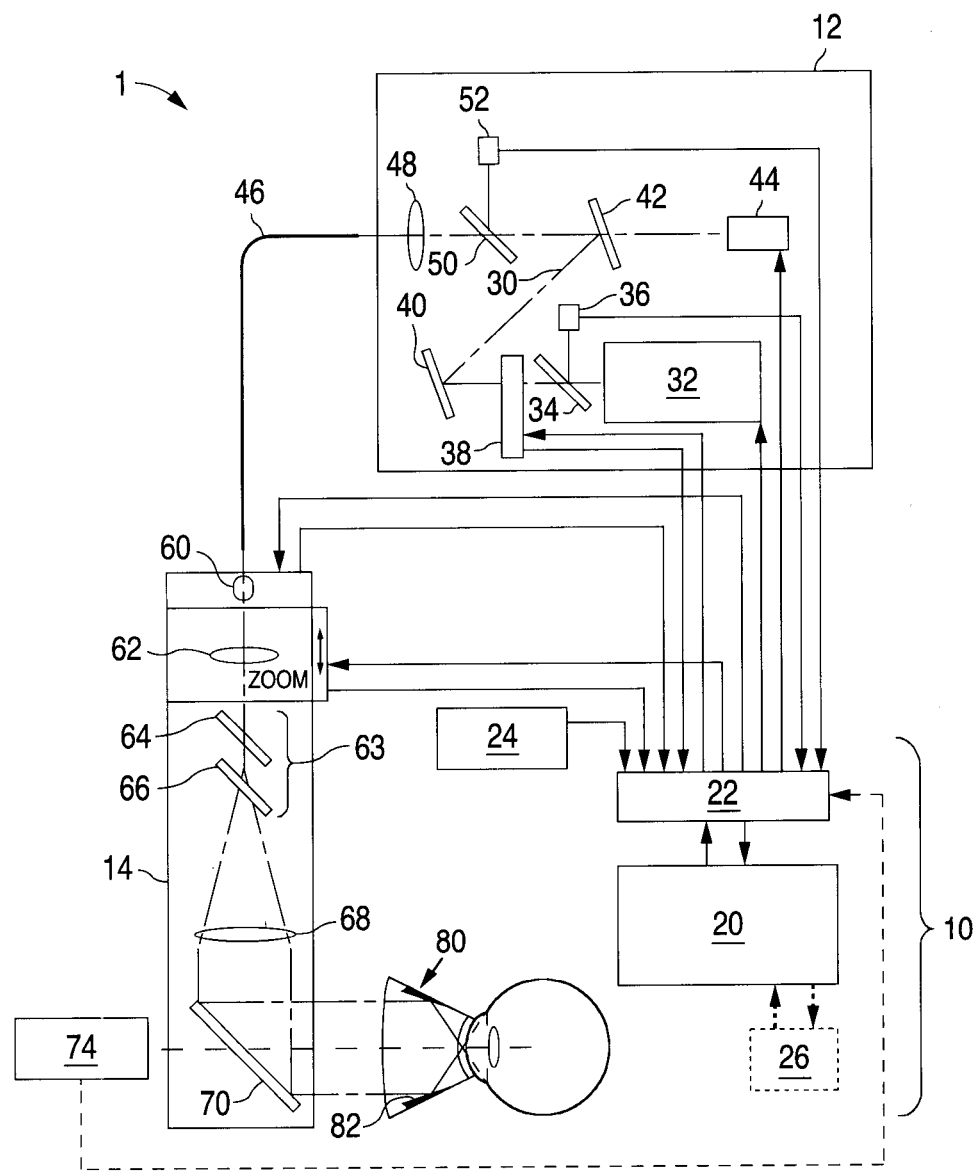
FIG. 2 is a schematic diagram illustrating an alternate embodiment of the system of FIG. 1, specifically for trabecular meshwork treatment.

FIG. 2 shows an alternate embodiment of the system 1, which is particularly suited for the treatment of the trabecular meshwork (TM). Here the ophthalmic contact lens of FIG. 1 is replaced with a gonioscopic lens 80 with reflective side surfaces 82, which are optimized for directing the light at an acute angle towards the TM.

Inherent flexibility of the scanned light beams enables many desired clinical possibilities. Some or all of system 1 may be mounted directly onto, among other things, an ophthalmic visualization tool such as a slit lamp biomicroscope, indirect ophthalmoscope, fundus camera, scanning laser ophthalmoscope, or optical coherence tomography system. Visualization device 74 may be employed to display the results of dosimetry pattern P on the graphic user interface 26 for physician review and input. Alternately, system 1 itself may be configured to assess the resultant lesions directly by using visualization device 74, in order to create input for an inference algorithm or heuristic to determine system settings for a given desired clinical result. Regardless of the degree of automation, such desired clinical results may be the degree of lesion intensity (darkness) or color or size, or the spatial selectivity of the treatment, and may be realized by varying one or more dosage parameters (i.e. size, power density, and/or pulse duration) of the light beam.

Once the physician or the system 1 determines the desired treatment conditions from the lesions generated by the delivery of the dosimetry pattern P onto the target tissue, system settings that dictate the dosage parameters of the beam at any given location (i.e. pulse duration, power density and/or spot size) can be set to produce the desired clinical result during subsequent treatment. That subsequent treatment can take the form of a single spot treatment, or a pattern P of treatment light produced in a similar manner as the dosimetry pattern P (i.e. a plurality of fixed spots, one or more continuous scans resulting in one or more straight or curved line segments, or a combination of both). It should be noted that the dosage parameters during treatment can be set to produce clinical results that match or do not match one of the visible lesions produced by the delivery of the dosimetry pattern P. For example, if the desired clinical result is to treat tissue with light without producing a visible lesion, then the treatment dosage parameters would be set to just below those that produced the lightest visible lesion from the dosimetry pattern P.

Figure 3:
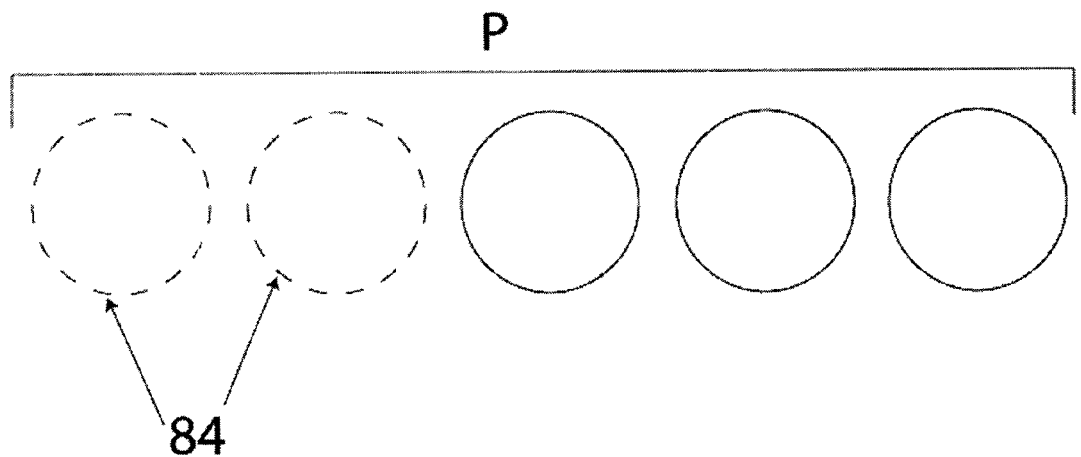
FIG. 3 is a schematic diagram illustrating an embodiment of the dosimetry pattern formed by discrete pulses.

FIG. 3 shows an example of a dosimetry pattern P that is a linear array of fundamental spots 84 in which the pulse duration varies from spot to spot (e.g. progressively increasing from left to right), while the power density remains constant. In this example, each of the spots results in the formation of a visible or non-visible lesion. The first and second spots of this exemplary five-spot dosimetry pattern P are shown with dotted outlines to illustrate that they did not produce visible lesions. Based upon observed character of the lesions, the physician or system may then choose treatment dosage parameters in a number of ways. First, treatment dosage parameters can be set to match those dosimetry pattern dosage parameters that created one of the lesions exhibiting the desired clinical result. This could also be as simple as the physician or system identifying the desirable lesion in the dosimetry pattern (e.g. via the GUI 26), and the system setting the treatment dosage parameters to match those dosimetry pattern dosage parameters that generated that lesion. Second, treatment dosage parameters can be set to match dosage parameters extrapolated from the dosimetry dosage parameters that created one or more of the lesions of interest (e.g. dosage parameters in-between those that created two different lesions, or dosage parameters below those that generated the lightest lesion to generate non-visible treatment lesions). Third, the physician or system can simply identify the number of visible lesions generated by the dosimetry pattern. Based on this input, the system can determine the threshold of dosage parameters needed to generate visible changes in tissue, and adjust the system dosage parameters to produce the desirable clinical result.

Because some spots 84 may not be visible, it is preferable (but not necessary) to index the dosimetry pattern P starting from the end of the pattern formed by the highest dosimetry settings, which are those most likely to cause visible lesions. To minimize potential damage during the dosimetry test, it is preferably in many clinical applications to use pulse durations and power densities for dosimetry pattern P that are less than or equal to the expected therapeutic pulse, so that the applied energy will be below the expected therapeutic energy. For better statistical predictability, dosimetry pattern P may include several identical rows, where an average result from the various rows are used to determine the treatment dosage parameters.

Figure 4:
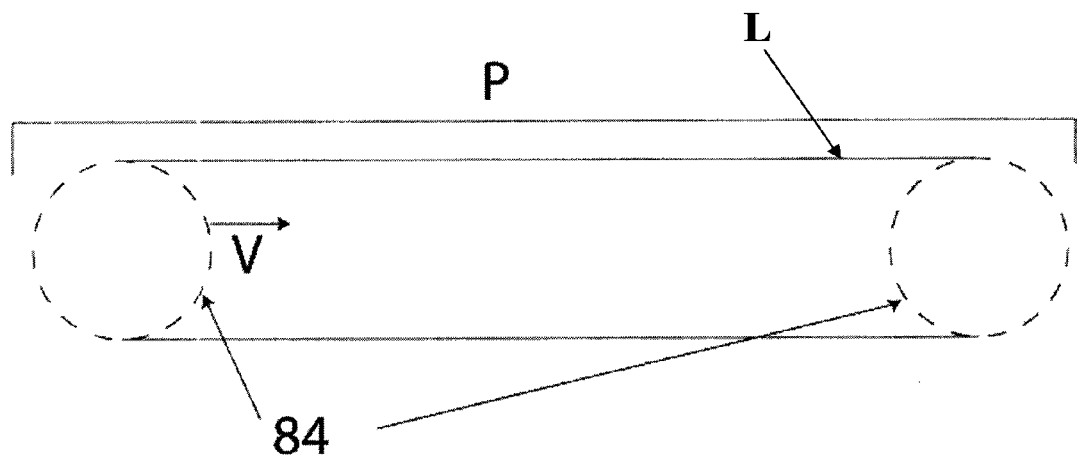
FIG. 4 is a schematic diagram illustrating an alternate embodiment of the dosimetry pattern formed by a continuous scan.

FIG. 4 shows an alternate embodiment, where the dosimetry pattern P is formed by a single continuous scan of a light spot 84 to create a line L. The velocity V of spot 84 varies along line L, causing the beam to dwell on different tissue locations within dosimetry pattern P for different amounts of time (i.e. varying the pulse duration on the tissue underneath line L). Alternately, the power density and/or spot size can be varied along line L, also resulting in a variable exposure along line L. Similar to the example of FIG. 3, treatment results may be derived from the position within dosimetry pattern P, in lieu of choosing a discrete spot number with the desirable appearance or reporting the number of visible lesions. Thus, the patient's tissue response may be judged, and the desired dosimetry prescribed empirically. The concurrent display of the aiming light can facilitate this distinction.

Figure 5:
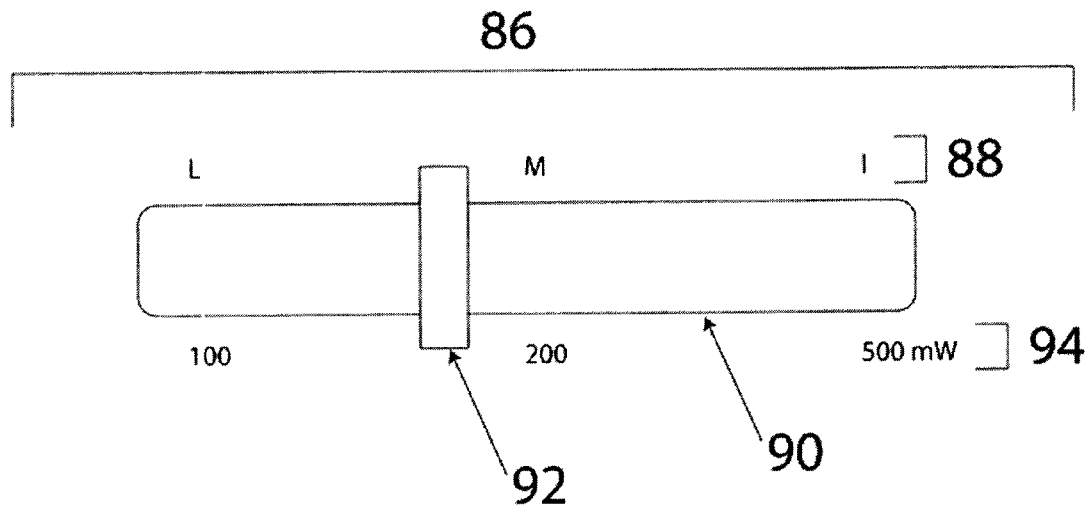
FIG. 5 is a system GUI display indicator that indicates the character of the lesion based upon the results of the dosimetry pattern and selected pulse parameters.

Software, firmware and/or hardware in system 1 can include a phenomenological lookup table based on experimental measurements of the retinal coagulation at various laser power densities, pulse durations and spot sizes. For example, once the dosimetry pattern P has been applied, and the number of visible legions resulting therefrom identified, the graphic user interface 26 can display an "expected lesion" indicator 86, on an indicator bar 90, as shown in FIG. 5. A further input by the physician could be the position of a sliding bar 92 along indicator bar 90 which represents a desired clinical result (e.g. the clinical degree of the lesion). The values 88 in this example reflect the desired degree of the burn within the lesion: Light, Medium, and Intense. The values 94 under the bar may be extracted by the software, firmware and/or hardware from a lookup table based on the laser power density, spot size, pulse duration and the threshold of lesion visibility established by the dosimetry pattern scan.

Figure 6:
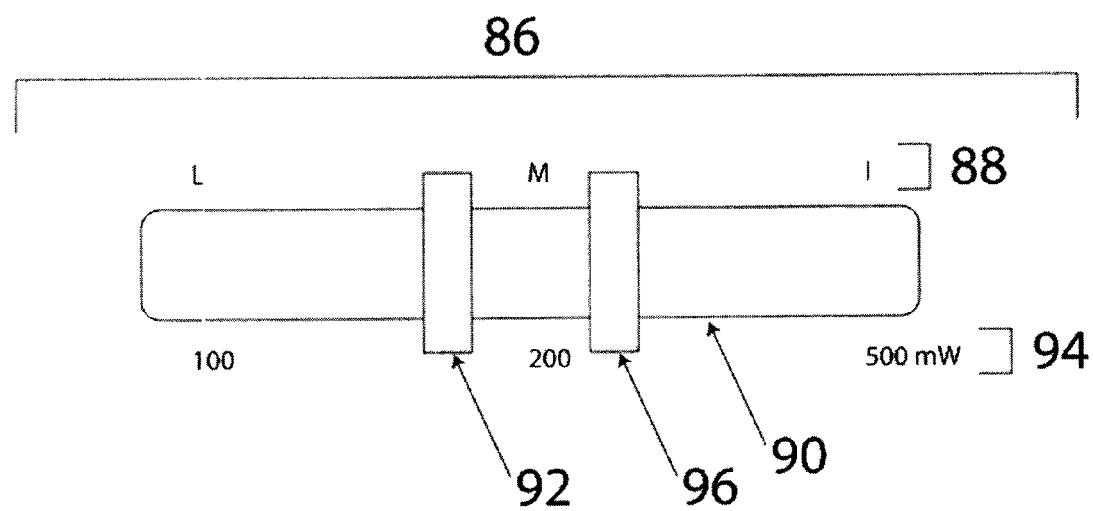
FIG. 6 is an alternate embodiment of the system GUI display indicator, based upon the ongoing results of the treatment.

FIG. 6 shows an alternate embodiment of indicator 86, where the system includes an inference engine. For example, after the application of a therapeutic pattern, the graphic user interface 26 displays an "observed lesion" slider bar 96 that is initially set to the same position as the "desired lesion" slider bar 92 of FIG. 5. When the lesions are not as predicted by the results of dosimetry pattern P, the user could change the "observed lesion" slider bar 96 to reflect the actual clinical result just produced by system 1. This would allow for the ongoing adjustment of the treatment dosage parameters without the need for utilizing further dosimetry patterns P. This automatic introduction of experimental data continuously to the database with physician feedback regarding the actual results will help in building a larger and more confident lookup table. Of course, if the outcome of the therapy is observed to be satisfactory, the physician can ignore the "observed lesion" control 86 and continue using the settings as they are. Furthermore, if the physician changes the spot size, the laser power density and/or pulse duration, the position of bar slider 92 may be automatically recalculated based on the model or a look-up table to keep the lesions consistent. When visualization is integrated into the system 1, and used as an input for system 1, this may be done during treatment using the same schemes previously discussed.

Figure 7:
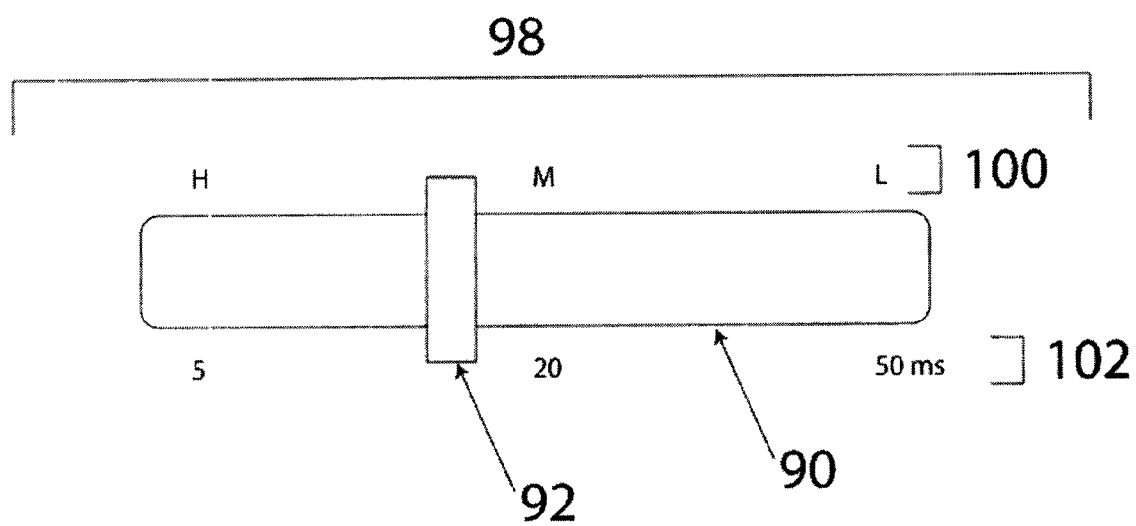
FIG. 7 is an alternate embodiment of the system GUI display indicator for selecting the spatial selectivity of the lesion, based upon the results of the dosimetry pattern.

FIG. 7 shows a control/indicator 98 that simplifies the creation of ophthalmoscopically invisible lesions from the results of applying the dosimetry pattern P to target tissue. Control/indictor 98 consists of an indicator bar 90, similarly to that in FIG. 6. However, in this example, the degree of spatial selectivity is the value controlled. Experiments by the inventors have shown the once the ophthalmoscopically visible threshold for creating a lesion is established, one may keep the power density fixed, and decrease the pulse duration to better localize the extent of the lesion. Unexpectedly, animal models have shown that this can be as straightforward as adjusting power density to achieve a visible burn at 20 ms, and then reducing the pulse duration to 5 ms in order to produce lesions whose axial extent is confined to the RPE and photoreceptor outer-segments. Once the lesion threshold is identified by applying the dosimetry pattern P, the axial extent of the lesion can be selected by reducing the pulse duration. The relationship between pulse duration and the extent of thermal damage is not linear. The use of control 98 simplifies operation by providing the user an efficient means by which to select the spatial selectivity (or, axial extent of the lesion) by moving a slider bar 92 in a manner similar to that described for FIG. 5. Here, however, the values 100 and parameters 102 reflect the spatial selectivity and the pulse duration, respectively. Spatial selectivity has been denoted by the terms High (H), Medium (M), and Low (L). High selectivity lesions are more confined than low selectivity lesions.

Figure 8:
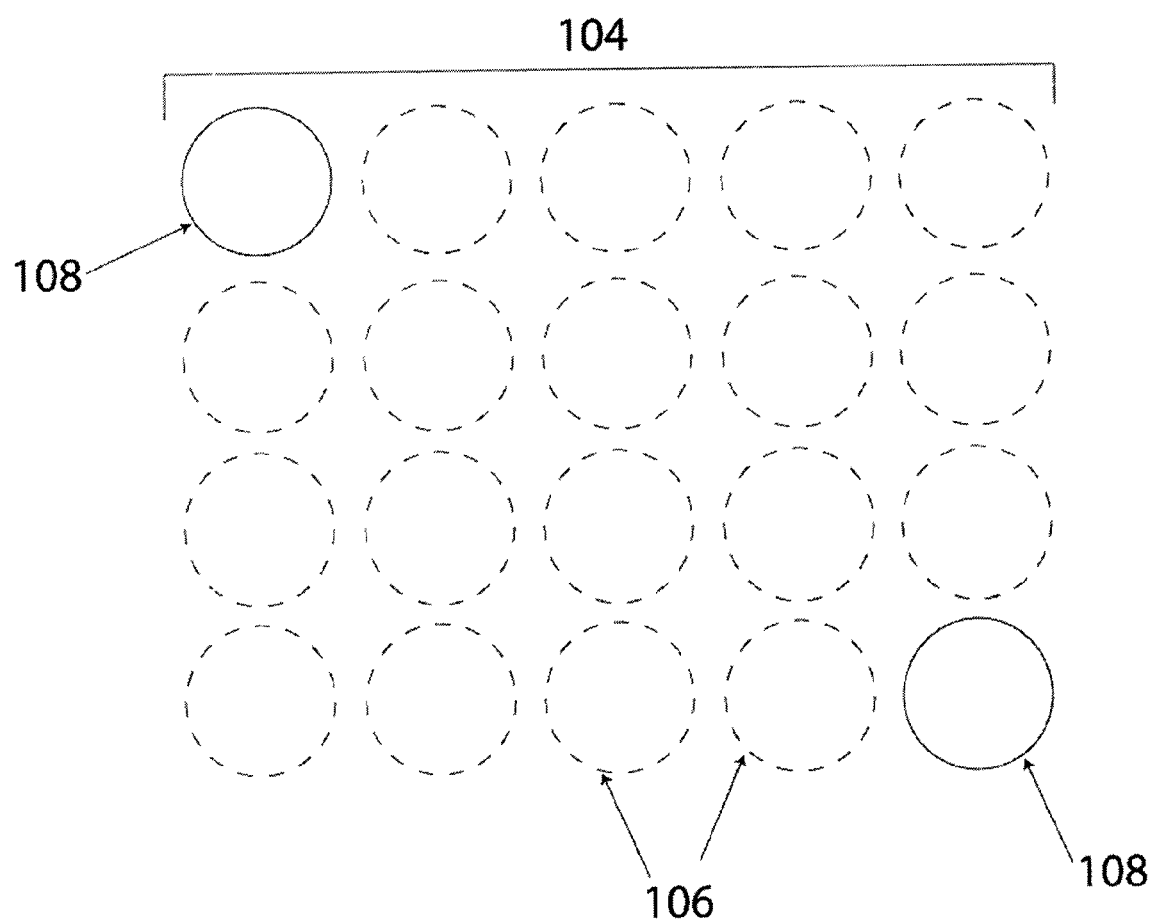
FIG. 8 is a schematic diagram showing the use of visible fiducial lesions to indicate the boundary of a pattern of ophthalmoscopically invisible lesions.

FIG. 8 shows the use of a mixture of ophthalmoscopically visible and invisible lesions to produce patterns that are easy to place adjacent to each other. A therapeutic pattern 104 may include various lesions corresponding to ophthalmoscopically invisible lesions 106 (dashed outlines) to perform minimally traumatic therapy, and visible lesions 108 (solid outlines) at the periphery of the pattern for producing fiducial marks to align the next pattern. These visible lesions 108 may be of longer pulse duration and/or higher power density, than ophthalmoscopically invisible lesions 106, for example.

These fiducial marks will allow for the precise placement of adjacent patterns without causing large amounts of otherwise undue damage. Of course, other configurations and arrangements of fiducial marks are possible. By first determining the threshold of dosage parameters needed to generate visible changes in tissue via the application of the dosimetry pattern P as described above with reference to FIG. 3, the system dosage parameters necessary to generate visible lesions 108 can be determined.

It is to be understood that the present invention is not limited to the embodiment(s) described above and illustrated herein, but encompasses any and all variations falling within the scope of the appended claims. For example, while the preferred light sources for generating the dosimetry pattern P and the treatment beam/pattern are lasers, any appropriate light source can be used to generate the light beams for dosimetry pattern P and the treatment beam/pattern. The functionality of control electronics 20 can be hardware only, and/or include functionality found by software and/or firmware running thereon as well.

What is claimed is:

1. A system for treating ophthalmic target tissue using a treatment pattern of lesions, wherein the treatment pattern comprises a first sub-pattern of lesions and a second sub-pattern of lesions, the system comprising:
    a light source for generating a beam of light towards a beam delivery unit;
    the beam delivery unit configured to deliver the beam of light to the ophthalmic target tissue, the beam delivery unit including a scanner unit configured to deflect the beam of light; and
    a control unit operatively coupled to and configured to control at least one of the light source and the beam delivery unit to:
        deliver the beam of light to the ophthalmic target tissue, wherein the delivery creates a first sub-pattern of lesions on the ophthalmic target tissue, the first sub-pattern including:
            a plurality of ophthalmoscopically invisible lesions, and at least one ophthalmoscopically visible lesion; and
    a visualization device configured to identify an ophthalmoscopically visible lesion from the first sub-pattern of lesions, wherein the control unit is further configured to control a least one of the light source and the beam delivery unit to:
        after creating the first sub-pattern, align the beam of light based on the identified ophthalmoscopically visible lesion from the first sub-pattern, and create the second sub-pattern of lesions on the ophthalmic target tissue using the aligned beam of light,
        wherein the ophthalmoscopically visible lesion from the first sub-pattern indicates an end of the first sub-pattern, and
        wherein the second sub-pattern is adjacent the first sub-pattern but does not overlap the first sub-pattern.

2. The system of claim 1,
    wherein the control unit is further configured to adjust a pulse duration of the beam of light, and
    wherein the plurality of ophthalmoscopically invisible lesions are formed using a shorter pulse duration of the beam of light and the at least one ophthalmoscopically visible lesion is formed using a longer pulse duration of the beam of light.

3. The system of claim 1,
    wherein the control unit is further configured to adjust a power density of the beam of light, and
    wherein the plurality of ophthalmoscopically invisible lesions are formed using a lower power density of the beam of light, and the at least one ophthalmoscopically visible lesion is formed using a higher power density of the beam of light.

4. The system of claim 1,
    wherein the control unit is further configured to adjust a pulse duration and a power density of the beam of light, and
    wherein the plurality of ophthalmoscopically invisible lesions are formed using a shorter pulse duration and a lower power density of the beam of light, and the at least one ophthalmoscopically visible lesion is formed using a longer pulse duration and a higher power density of the beam of light.

5. The system of claim 1, wherein:
the first sub-pattern includes a first row of lesions.

6. The system of claim 2, wherein:
the ophthalmoscopically visible lesion from the first sub-pattern that indicates an end of the first sub-pattern is the first lesion in the first row of lesions.

7. The system of claim 2,
    wherein the first sub-pattern includes at least two rows of lesions,
    wherein a first row of the at least two rows of lesions is aligned above a second row of the at least two rows of lesions,
    wherein the ophthalmoscopically visible lesion from the first sub-pattern that indicates an end of the first sub-pattern is at one end of the second row of lesions.

* * * * *